United States Patent [19]

Doundoulakis et al.

[11] Patent Number: 5,066,228
[45] Date of Patent: Nov. 19, 1991

[54] SALIVA EJECTOR

[76] Inventors: George J. Doundoulakis, 2498 Kayron La., North Bellmore, N.Y. 11710; James H. Doundoulakis, 110-20 71st St., Forest Hills, N.Y. 11375

[21] Appl. No.: 571,182

[22] Filed: Aug. 23, 1990

[51] Int. Cl.$^5$ .................... A61C 17/06; A61C 17/14
[52] U.S. Cl. ..................................... 433/91; 433/95
[58] Field of Search .................. 433/91, 95, 96, 92, 433/93; 604/131, 133

[56] References Cited

U.S. PATENT DOCUMENTS

| 3,520,300 | 3/1967 | Flower | 433/91 |
| 3,541,583 | 4/1967 | Deuschile | 433/96 |
| 4,015,336 | 4/1977 | Johnson | 433/95 |
| 4,767,404 | 8/1988 | Renton | 604/48 |

Primary Examiner—John J. Wilson
Assistant Examiner—Cindy A. Cherichetti

[57] ABSTRACT

One object of the present invention is to provide a saliva ejector tip (3) having holes (6) on a recessed flat surface (4) for providing additional hole area than is available in conventional ejector tips, and away from the soft tissue, where they can cause injurious sucking.

The other object is to provide a saliva ejector capable of self controlling the total area of holes by using the strength of the internal vacuum to displace a movable portion (17) of the tip, so that holes (12) and (13) are aligned for increasing the total hole area. Such an increase expedites the rate of removal of fluids so that subsequent inflow of air reduces the vacuum strength, and thereby, helps releasing the soft tissue that may have been sucked up by other holes. Upon lowering of the internal vacuum, the movable portion of the tip returns to its normal position.

6 Claims, 1 Drawing Sheet

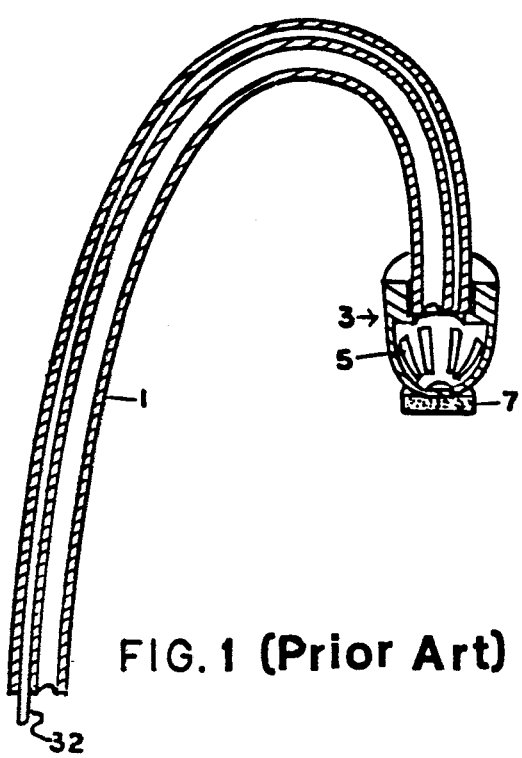
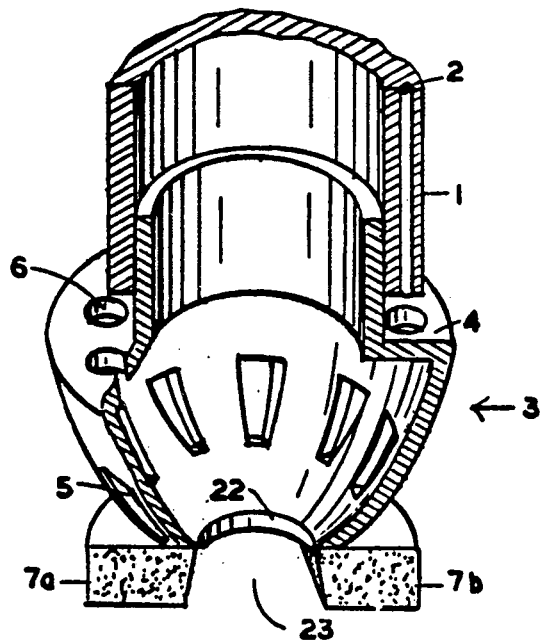
FIG. 1 (Prior Art)
FIG. 2
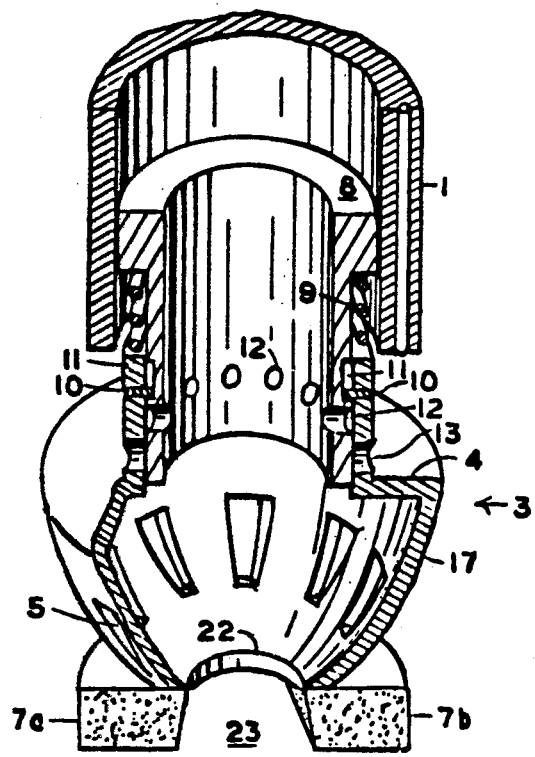
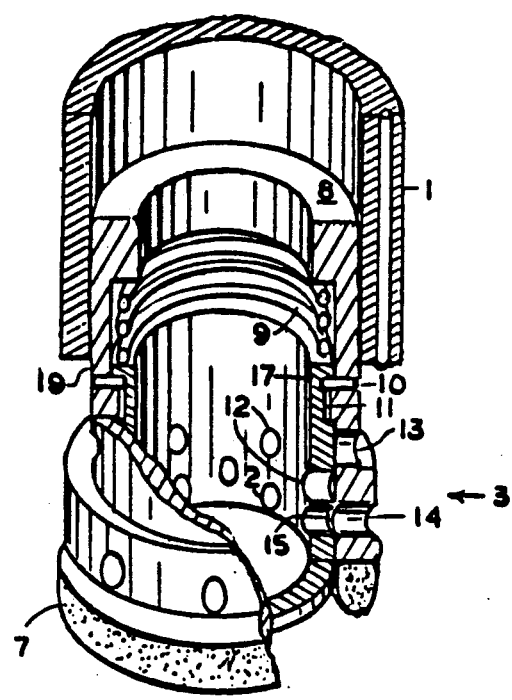
FIG. 3
FIG. 4

SALIVA EJECTOR

TECHNICAL FIELD

The present invention relates to ejectors and in particular to improved tips of saliva ejectors, used during dental treatment.

BACKGROUND ART

Saliva ejector are used by the dentists to provide continued ejection of saliva out of the mouth of patients during dental treatment. The most common type of ejector is portrayed in FIG. 1. It comprises a flexible tube which can be bent to provide a hook over the lower lip of the patient. The hook is structurally maintained by a copper wire, which is built inside the wall of the flexible tube. Internally the flexible tube provides a channel for moving away waste liquids entering the tip. The flexible tube usually provides, at one end, a standard diameter for plugging directly into the tube which extends from the machine generating the vacuum and connecting with the evacuation system.

At the other end of the flexible tube fits the ejector tip as shown in FIG. 1, which generally provides openings through which saliva, blood, water, and other waste products from the patients' mouth pass into the flexible tube.

Various designs of saliva ejector tips are being commercially offered and are tried by the dentists in the hope of finding a satisfactory ejector. The criteria are mainly three: (1) not to suck up the patients floor of the mouth, tongue or other sensitive tissue inside the mouth; (2) not to clog up easily; and (3) to provide a standard diameter at the end so that it can plug into the machine's tube, without the need of a home-made adaptor.

One type of tip provides a coiled tubule having its end open and further having holes in between the convolutions so that the tongue and soft tissue of the mouth can be protected. The drawbacks of this design are: (1) the opening at the end is positioned away from the floor of the mouth where porcelain and metal solid particles accumulate; (2) the internal friction is excessive because of its small diameter and relatively long length, thereby providing slow service while being susceptible to clogging by small particles; and (3) it does not provide standard diameter at the end.

The conventional type, shown in FIG. 1, also provides drawbacks, particularly in the area of sucking up soft tissue and clogging.

From the engineering point of view the sucking force F that is applied by a hole at the tip to the soft tissue of the mouth, expressed in pounds, is equal to $$F = (P_i - P_a) \times A \qquad (1)$$

where: $P_i$ and $P_a$ represent the pressure inside the flexible tube and atmospheric pressure, respectively, expressed in pounds per square inch, and A is the area of the hole expressed in square inches.

To keep the force F small, the holes must be kept small; but in this case there is more of a change for clogging. It may be noted that the above force F can be maintained, despite the fact that other holes at the tip may be open and conducting waste. This is because the vacuum $(P_i - P_a)$ can be easily maintained by a strong source, as long as the flow of waste liquids remains slow. The low rate of flow is due to the resistance contributed by the viscosity of the waste fluids as they flow through the walls of the holes and the flexible tube. Once a hole grabs the tissue, it will hold on to it as long as the force F remains enough to overcome the low skin tension force.

A desirable tip, therefore should provide sufficient hole area for the fluid to be processed quickly; after the fluid is sucked air follows at a faster rate, having a much lower viscosity. Air quickly increases the internal pressure $P_i$, thereby reducing the value of F to less than skin tension so that the soft tissue, if held by other holes, can be released. It is apparent, therefore, that more hole area is needed at the tip with a large portion of such area being recessed away from the region of direct contact with the soft tissue.

Still another desirable feature would be for the tip to have a large opening at the lower end and near the region where hard particles, such as grinds of teeth, porcelain and metal usually fall. Provision, however, must be made to protect the patient's tissue f25 m a substantial force F, which such a large hole would provide.

A third desirable feature in a saliva ejector tip would be to provide control of the total area of openings versus the force F itself, so that a large F, indicating substantial sucking of soft tissue, could trigger a process of automatic increase in area not in contact with soft tissue.

DISCLOSURE OF THE INVENTION

On the basis of the conclusions reached above, the invention provides for a plurality of additional holes at a level further up from the location of the conventional holes, and on a surface recessed away from the soft mouth tissue.

In Embodiment A, illustrated in FIG. 2, a tip plugged on to a standard flexible tube is shown to provide, besides the holes shown in FIG. 1, additional holes on a surface, substantially at right angle to the side wall of the tip recessed away from the soft tissue of the mouth, for speeding up the suction of the waste fluid so that air can enter the tip to raise the pressure $P_i$ and lower the suction force F. At the same time a round hole is provided at the lower end of the tip with a foam cushion split in two parts, one on each side of the hole, for keeping the soft tissue skin away from the hole, while allowing an open channel for hard wastes to reach the hole.

Embodiment B illustrated in FIGS. 3 and 4 provides for self control means, automatically causing additional holes to be opened if the vacuum $(P_i - P_a)$ exceeds a predetermined value, determined by the stiffness of a spring. According to this embodiment the tip is comprised of two parts, a stationary part, which is plugged into the standard flexible tube connected to the machine providing the vacuum, and a second part, movably supported by the first part. A weak spring of predetermined stiffness urges the movable part downwardly, away from the stationary part. When the internal vacuum $(P_i - P_a)$ exceeds the force of the spring, as a consequence of too much fluid or the soft tissue being sucked in by the holes, the atmospheric pressure operates on the outside surface of the tip to displace the moving part upwardly against the force of the spring. During such a displacement, previously non-aligned holes in the two parts become aligned to allow additional fluid flow. As soon as the fluid is processed and the internal vacuum diminished, usually due to intake of air, the spring pushes the lower part back to its normal position. An advantage of a self regulating saliva ejector is that when the amount of waste fluid is small and the holes on the lower level of the tip are sufficient to process the fluid and there is no suction of tissue, a large hole at the end of the tip can be more forceful in removing hard particles when the upper level holes remain shut. But if the lower level holes are covered by skin and/or fluid the tip can itself regulate the opening of additional holes to cause release of the soft tissue.

Two species of Embodiment B are illustrated in FIGS. 3 and 4. Both species perform in a similar manner, as described above. However, they differ in topology. The species of FIG. 3 has its movable part disposed outside the stationary part; while in the species of FIG. 4 the movable part is disposed inside the stationary part. Another difference is that the lower level holes, as well as a round hole at the end of the tip in the species of FIG. 3 remain continuously open. In the species of FIG. 4 all side holes are controlled, and there is no hole at the end of the tip. The area of all holes, therefore can be controlled as a function of the value of the vacuum $(P_i - P_a)$.

Accordingly, it is the main object of this invention to provide a saliva ejector tip with additional hole area than is available in presently commercially available tips, for the purpose of faster processing of the waste fluid; thereby, as air will follow, it will cause the internal vacuum to be reduced, allowing any soft tissue that has been sucked by holes to be released.

It is a further object of this invention to provide an improved shape to a saliva ejector tip allowing additional holes to be recessed from the vertical side of the tip, away from direct contact with the skin of soft mouth tissue.

Another object of this invention is to provide a additional hole at the lower end of the tip with skin protective foam cushioning material, for removing hard particles such as grinds of teeth and metals.

Another object of this invention is to provide a saliva ejector with the capability of self adjusting the area of the holes, as a function of the magnitude of the internal vacuum. Self regulation of the area to be accomplished by said ejector being comprised of two parts, an upper stationary part which can be rigidly plugged into the standard flexible tube connected to the machine generating the vacuum, and a lower part, movably held by the stationary part. The latter part being urged by a weak spring downwardly, until the internal vacuum overcomes the stiffness of the spring for the atmospheric pressure to displace said movable part upwardly; thereby bringing in alignment holes in the two parts for increasing the flow.

Other objects and features of the invention will be discussed as the description of the particular physical embodiments are selected to illustrate the invention processes. The various novel features that characterize the invention are pointed out particularly in the claims annexed to and forming a part of this specification. In addition, for a better understanding of the invention, its operating advantages and specific objects attained by its use, references are made to the accompanying drawings and descriptive matter in which preferred embodiments of the invention are illustrated and described.

The invention is illustrated diagrammatically in the accompanying drawings by way of examples. The diagrams illustrate only the principles of the invention and how these principles are employed. It is, however, to be understood that the purely diagrammatic showing does not offer a survey of other possible constructions, and a departure from the constructional features, diagrammatically illustrated, does not necessarily imply a departure from the principles of the invention. For example, the shape of the ejector for providing recessed surfaces for the holes to stay away from the skin of soft tissue in the mouth may be rendered in various ways. Also the edge of the holes may be chosen from several shapes, such as round, rectangular, etc.

It is, therefore, to be understood that the invention is capable of numerous modifications and variations to those skilled in the art without departing from the spirit and scope of the invention.

In the accompanying drawings, forming part hereof, similar reference characters designate corresponding parts.

BRIEF DESCRIPTION OF DRAWINGS

The details of our invention will be described in connection with the accompanying drawings in which:

FIG. 1 is an isometric, cross-sectional elevation view, showing a conventional saliva ejector comprising a flexible tube bent into a hook and ending with a conventional tip.

FIG. 2 is an isometric, mostly cross-sectional, elevation view of a novel saliva ejector tip, providing additional holes along a recessed surface, with portions cut-away for clarity.

FIG. 3 is an isometric, mostly cross-sectional, elevation view of a novel saliva ejector tip, providing automatic control to the amount of open hole area, with portions cut away for clarity.

FIG. 4 is an isometric, mostly cross-sectional, elevation view of another species of saliva ejector similar to that shown in FIG. 3, also providing automatic control on the open area of the holes on the tip, with portions cut away for clarity.

BEST MODE OF CARRYING OUT THE INVENTION

All species of saliva ejectors presented in FIGS. 1 through 4 employ the standard flexible tube 1 shown in FIG. 1. Flexible tube 1 is commercially available with a low stiffness wire 32, such as copper wire, built in its wall so that the flexible tube can retain a bent, and further having a standard opening at the end so that it can be adapted to the standard tube of the machine providing the vacuum. The flexible tube 1 is bent by the dentist to form a hook for support of the ejector over the lower lip of the patient. A tip 3, attached at the other end of the flexible tube provides holes 5 for conducting the waste fluid. The tip 3 is occasionally provided with a foam cushion 7, for patient's comfort. The conventional tips of this type do not provide a hole at the end of the tip so that the cushion 7 is not used to prevent sucking of the skin of the mouth by the hole.

Embodiment A provides a tip 3, shown in FIG. 2, having a standard diameter at one end so that it can be adapted to the standard flexible tube 1. Tip 3 besides providing holes 5 as conventional tips do, it further provides additional holes 6, located at a recessed surface 4. The surface 4 is so provided as to keep the additional holes 6 away from the skin of the soft tissue of the mouth. An additional hole 22 is provided at the end of the tip 3 near the region where hard particles of tooth and metal grinds usually accumulate. The hole 22 will preferably be large enough not to be clogged by chips of these materials. Two pieces of foam cushion 7a and 7b are cemented one on each side of the hole 22 in a way that a channel 23 is left open for the passage of fluid wastes and hard particles, while keeping the soft tissue skin of the mouth away from the hole 22 to avoid sucking of the skin by the hole 22.

Referring now to the embodiment B and in particular to the species illustrated in FIG. 3, the saliva ejector tip 3 comprises two parts, a stationary upper part 8 with a standard diameter at the end so that it can be adapted on to the standard flexible tube 1, and a lower part 17, movably supported onto the stationary part 8. A spring 9, of predetermine stiffness, is urging the two parts 8 and 17 apart, at which position holes 12 and 13 on the two parts, respectively, are not aligned, and, therefore, are not conducting fluid. However, when there is an abundance of fluid and/or sucking of the mouth skin, causing the vacuum ($P_i - P_a$) to increase in magnitude, the atmospheric pressure acts upon the outside surface of the part 17, causing it to be displaced against the force of the spring 9. The additional holes 12,13 then are aligned and become conductive, processing the fluid at a faster rate. As soon as the level of fluids is lowered, air is sucked in, reducing the vacuum and the force F, and causing the release of the skin. The movable part 17 is then pushed by the spring 9 back to its normal position. Respective rotation of the two parts 8 and 17 is prevented by pins 10 of part 17, the tips of which can move along a groove 11 on the part 8, and which can interfere with the sides of the grooves 11 when the two parts are urged to rotate with respect to each other.

It may be noted that the movable part 17 is a similar design as that of FIG. 2, except that the holes 6 have been replaced by the holes 12,13. The hole 22 with the cushions 7a and 7b remain as described in connection with FIG. 2.

The species of the tip 3 shown in FIG. 4, also belonging to Embodiment B, do provide self control of the total area of holes as a function of the vacuum value ($P_i - P_a$). The stationary part 8 provides proper diameter for the tip 3 to be adapted to a standard flexible tube 1. Part 8 here extends all the way down to the end of the tip 3, where a foam ring cushion 7 is cemented for the patient's comfort. Part 8 provides two rows of holes, 13 and 14. A second part 17 is loosely and movably supported inside the part 8. A weak spring 9 of predetermined stiffness is urging the part 17 apart from part 8. The extent part 17 can move is determined by the length of a grooves 11 in which the end of a pins 10 can slide. The same groove/pin arrangements prevent the two parts 8 and 17 from rotating with respect to each other. A row of holes 12 are not normally aligned with the holes 13. These holes, however become aligned when the magnitude of the internal vacuum ($P_i - P_a$) exceeds the resistance of the spring 9, in which case the part 17, under the influence of the atmospheric pressure, is displaced upwardly. While part 17 remains at its extended position the holes 14 may be arranged to align or not with holes 15. As shown in FIG. 4 the lower holes 15 may be arranged to alternate at two height levels so that half of them will be aligned at one extreme position and the other half at the other extreme position of the movable part 17. In this manner half the holes 15 will be fully conducting with part 17 at is normal position away from the part 8, the other half will be fully conducting with the part 17 moved at its extreme position upwardly, and all holes may be partially conducting with the part 17 partially moved upwardly. This arrangement can serve to self release the skin of soft tissue if sucked in by the normally conducting lower level holes. As the driving force for a displacement of the part 17 in this species is provided by the action of the atmospheric pressure along the area of the bottom of part 17, this area is, preferably, remaining covered, with no hole provided on it.

I claim:

1. An improved saliva ejector tip for providing more efficient ejection of fluids and waste products from a patient's mouth during dental treatment, while reducing the likelihood of sucking up soft tissue; such tip being connected to vacuum-generating equipment and disposal plumbing via a flexible tube, usually bent into a hook for support over a patient's lower lip, comprising:

a substantially cylindrical end adaptor section, circumferencially disposed at an upper portion of said ejector tip, for joining said tip with the flexible tube; a substantially hemispherical cavity kept under partial vacuum by the vacuum generating equipment; said cavity being perforated around its side wall for allowing entrance of waste products from a patient's mouth;

wherein said cavity further comprises:

a circumferencially externally disposed region radially recessed away from said hemispherical cavity's outer surface for providing holes, which cannot be reached by the mouth's soft tissue; such holes providing at least a predetermined minimum admittance to fluids and or air into said cavity when the perforations on the outer surface are clogged or suck on to soft tissues of the mouth; thereby, the vacuum inside said cavity being reduced, causing the soft tissue to be released;

a substantially round hole, centrally disposed at a lower portion of said cavity for admitting both fluid and solid wastes; said hole further comprising a pair of cushions disposed externally one on each side of said hole, forming a recessed region in the form of a channel for allowing free passage to both fluid and solid waste; such cushions made out of soft material for cushioning said tip at the soft tissue of the mouth and for protecting the tissue from being sucked in by said hole, as they provide protective ridges keeping the soft tissue at a distance; while such cushions allowing between them a free channel for waste fluid and solid material to reach and be admitted by said hole.

2. The saliva ejector tip according to claim 1, wherein said lower member and said spring means are circumferencially disposed outside said upper member.

3. The saliva ejector tip according to claim 2, wherein said lower member further comprises a substantially round hole centrally disposed at a lower portion of said lower member for admitting both fluid and solid wastes.

4. The saliva ejector tip according to claim 3, wherein said round hole is further comprising a pair of cushions disposed externally one on each side of said hole forming a recessed region in the form of a channel for allowing free passage to both fluid and solid waste; such cushions made out of soft material for cushioning said tip at the soft tissue of the mouth and for protecting the tissue from being sucked in by said hole, as they provide protective ridges keeping the soft tissue at a distance; while such cushions allowing between them a free channel for waste fluid and solid material to reach and be admitted by said hole.

5. An improved saliva ejector tip for providing more efficient ejection of fluids and waste products from a patient's mouth during dental treatment with reduced likelihood aspirating soft tissue; such tip being connected to vacuum generating equipment and disposal plumbing via a flexible tube usually bent into a hook for support over a patient's lower lip, comprising:
- a substantially cylindrical upper member serving as adaptor for rigidly joining said tip with the flexible tube;
- a lower member providing side wall openings for allowing waste fluid and secretions from the patients mouth into said ejector tip, said lower member being movably supported onto said upper member;
- spring means of a predetermined stiffness urging said lower member downwardly, away from said upper member; thereby said lower member is pushed away by said spring means when the pressure difference between inside and outside of said tip is small, and said lower member is being displaced by the action of outside atmospheric pressure upwardly, causing said spring to contract when the pressure difference increases as a consequence of excessive fluids and or soft tissue, intraorally filling the side wall openings;
- a pin/slot combination between said upper and said lower member for allowing said lower member to axially slide with respect to said upper member, while preventing relative rotation between the two members;
- radially directed hole means on said upper and said lower member; wherein said hole means on the upper and lower members are not aligned and, therefore, do not conduct waste fluids when said lower member is at a lower position away from the flexible tube; but said hole means become aligned to conduct fluids as said lower member moves upwardly as a consequence of increased vacuum force when the side wall openings are being filled with fluid and or soft mouth tissue; thereby such additional conduction of fluids through said hole means as they become aligned, causes a drop in pressure difference and helps release of the soft tissue.

6. The saliva ejector according to claim 5, wherein said lower member and said spring means are circumferencially disposed internally to said upper member.

* * * * *